United States Patent
Rumpca et al.

(10) Patent No.: US 11,730,588 B2
(45) Date of Patent: Aug. 22, 2023

(54) RADIOPAQUE ELEMENTS FOR SURGICAL HEART VALVES

(71) Applicant: Medtronic, Inc., Minneapolis, MN (US)

(72) Inventors: James L. Rumpca, Ramsey, MN (US); Molly Anne Berringer, Brooklyn Center, MN (US); Matthew W. Weston, Roseville, MN (US); Timothy R. Ryan, Minnetrista, MN (US); Timothy D. Groen, Rush City, MN (US)

(73) Assignee: Medtronic, Inc., Minneapolis, MN (US)

( * ) Notice: Subject to any disclaimer, the term of this patent is extended or adjusted under 35 U.S.C. 154(b) by 50 days.

(21) Appl. No.: 17/165,084

(22) Filed: Feb. 2, 2021

(65) Prior Publication Data

US 2021/0251750 A1    Aug. 19, 2021

Related U.S. Application Data

(60) Provisional application No. 62/978,453, filed on Feb. 19, 2020.

(51) Int. Cl.
*A61F 2/24* (2006.01)

(52) U.S. Cl.
CPC .... *A61F 2/2418* (2013.01); *A61F 2250/0097* (2013.01); *A61F 2250/0098* (2013.01)

(58) Field of Classification Search
CPC ........ A61F 2/24; A61F 2/2418; A61F 2/2412; A61F 2/2409; A61F 2250/0018;
(Continued)

(56) References Cited

U.S. PATENT DOCUMENTS 8,591,573 B2 * 11/2013 Barone .............. A61F 2/2418
                                                          623/2.19
9,089,422 B2    7/2015 Ryan et al.
(Continued)

FOREIGN PATENT DOCUMENTS

WO    2009094501    7/2009
WO    2014149295    9/2014
(Continued)

OTHER PUBLICATIONS

PCT International Search Report and Written Opinion for International Application No. PCT/US2021/016273 dated May 10, 2021 (10 pages).

*Primary Examiner* — Brian A Dukert
(74) *Attorney, Agent, or Firm* — Michael Best & Friedrich LLP

(57) ABSTRACT

Aspects of the disclosure include a prosthetic heart valve including a stent structure forming a plurality of commissure posts, a valve structure supported by the stent structure, a base supporting the stent structure and at least one radiopaque element positioned around the base. The radiopaque element can include a band extending around the base. In some embodiments the band is coiled. The band can optionally include a badge with an indicator specifying properties of the valve and viewable under fluoroscopy. In some embodiments, the radiopaque element is a badge that can have an indicator. The radiopaque elements of the disclosure increase ease and accuracy in the positioning of a percutaneously delivered replacement valve within a previously implanted valve of the disclosure.

8 Claims, 3 Drawing Sheets

(58) Field of Classification Search
CPC ........ A61F 2250/006; A61F 2250/0089; A61F 2250/0085; A61F 2250/0098
See application file for complete search history.

(56) References Cited

U.S. PATENT DOCUMENTS

| | | | |
|---|---|---|---|
| 9,504,566 B2* | 11/2016 | Guttenberg | A61F 2/2412 |
| 11,439,732 B2* | 9/2022 | Adamek-Bowers | A61F 2/2427 |
| 2009/0192591 A1 | 7/2009 | Ryan et al. | |
| 2010/0121436 A1 | 5/2010 | Tuval et al. | |
| 2014/0163673 A1 | 6/2014 | Bruchman et al. | |
| 2014/0277389 A1 | 9/2014 | Braido et al. | |
| 2015/0366664 A1 | 12/2015 | Guttenberg et al. | |
| 2016/0296324 A1 | 10/2016 | Bapat et al. | |
| 2017/0071735 A1 | 3/2017 | Guttenberg et al. | |
| 2017/0281340 A1* | 10/2017 | Guttenberg | A61F 2/2409 |
| 2017/0304049 A1 | 10/2017 | Hayes | |
| 2019/0321170 A1* | 10/2019 | Green | A61F 2/2409 |

FOREIGN PATENT DOCUMENTS

| | | |
|---|---|---|
| WO | 2015073815 | 5/2015 |
| WO | 2016100806 | 6/2016 |

* cited by examiner

RADIOPAQUE ELEMENTS FOR SURGICAL HEART VALVES

RELATED APPLICATIONS

This application claims the benefit of the filing date of U.S. Provisional Patent Application Ser. No. 62/978,453, filed Feb. 19, 2020, the entire teachings of which are incorporated herein by reference.

FIELD

The present technology is generally related to prosthetic heart valves including one or more radiopaque elements.

BACKGROUND

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

Although there have been advances in percutaneous valve replacement techniques and devices, there is a desire to be able to easily and accurately position percutaneously delivered replacement valves within a previously implanted valve. The present disclosure addresses problems and limitations associated with the related art.

SUMMARY

The techniques of this disclosure generally relate to prosthetic valves that are configured to provide features that promote optimal placement of a replacement heart valve. Such a placement of a replacement heart valve can be performed percutaneously or minimally invasively. Features of the disclosure can be used for aortic valve, mitral valve, pulmonic valve, venous, and/or tricuspid valve replacement. In some embodiments, the replacement heart valves of the disclosure are highly amenable to transvascular delivery using a transapical approach (either with or without cardiopulmonary bypass and either with or without rapid pacing). The methodology associated with aspects of the disclosure can be repeated multiple times, such that several prosthetic heart valves of the present invention can be mounted on top of or within one another, if necessary or desired. Techniques of the disclosure further include prosthetic valves whose sizes, valve position (aortic, mitral, pulmonic, tricuspid, etc.), or other information such as the model number or manufacture date of the valve can be identified from outside of a patient's body.

In one aspect, the present disclosure provides a prosthetic heart valve including a stent structure forming a plurality of commissure posts, a valve structure supported by the stent structure, a base supporting the stent structure and a radiopaque element positioned around the base.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to a prosthetic heart valve, the terms "distal" and "outflow" are understood to mean downstream to the direction of blood flow, and the terms "proximal" or "inflow" are understood to mean upstream to the direction of blood flow. Although the present disclosure has been described with reference to preferred embodiments, workers skilled in the art will recognize that changes can be made in form and detail without departing from the spirit and scope of the present disclosure.

Figure 1:
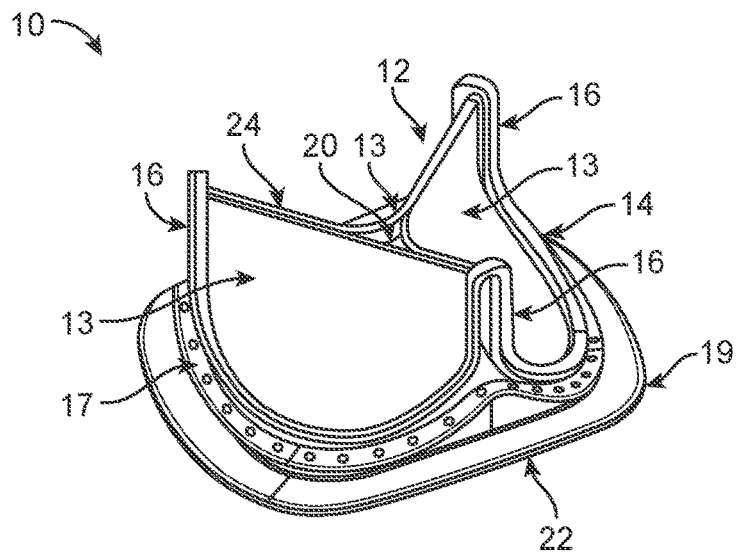
FIG. 1 is a perspective view of a prosthetic heart valve having an exposed base supporting a plurality of commissure posts and leaflets (a fabric covering encasing the prosthetic heart valve, as typically provided with prosthetic heart valves, is not shown for clarity).

Referring now initially to FIG. 1, by way of background, a prosthetic heart valve 10 is illustrated (a fabric covering encasing the heart valve, as typically provided with heart valves, is not shown for clarity). This valve 10 is a typical configuration of a valve that can be implanted within the heart of a patient, such as by suturing or otherwise securing the valve 10 into the area of a native heart valve of a patient. The native heart valves referred to herein can be any of the human heart valves (i.e., mitral valve, tricuspid valve, aortic valve, or pulmonary valve), wherein the type and orientation of an implanted (e.g., surgically implanted) prosthetic heart valve 10 will correspond with the particular form, shape, and function of the native heart valve in which it is implanted. It will be understood that embodiments of the disclosure can also be used to replace a failing or defective prosthetic heart valve that has been previously implanted within a native heart valve.

In the present example, valve 10 generally includes a valve structure 12 including a stent structure 14 from which multiple stent posts or commissure posts 16 extend (e.g., three commissure posts). The stent structure 14 is connected to and supported by an annular base 17. The valve structure 12 supports a plurality of leaflets 13 (e.g., three leaflets). All or a portion of the valve structure 12, including the stent structure 14 and stent posts 16, can be covered by a flexible covering (not shown for clarity), which may be a tissue, polymer, fabric, cloth material, or the like to which leaflets of the heart valve 10 are attached, such as by sewing. The valve 10 can optionally further include an annular sewing cuff 19 provided around the base 17. The stent structure 14 may, in some examples, be a wire form. Further, the internal structure of each of the stent posts 16 can be formed of a stiff but somewhat resiliently bendable material. This construction allows the stent posts 16 to be moved from the orientation shown in FIG. 1 to a deflected orientation by the application of an external force. Once this external force is removed or reduced, the stent posts 16 can then move back toward the orientation shown in FIG. 1. Alternatively, the stent posts 16 can be angled at least slightly toward or away from a central axis of the valve 10.

The valve structure 12 is generally tubular in shape, defining an internal area 20 (referenced generally) that extends from an inflow end 22 to an outflow end 24. The internal area 20 is essentially surrounded by the valve structure 12, and the leaflets 13 attached within the valve structure 12 selectively allow for fluid flow into and out of the lumen of the repaired heart valve in which it is implanted. That is, the internal area 20 is alternatively open and closed to the lumen of the repaired heart valve in which it is inserted via movement of leaflets 13. In some patients, the prosthetic heart valve 10 will be implanted using typical surgical techniques, whereby the sewing cuff 19 is sewn or attached to the annulus or valvular rim of a native heart valve. Alternatively, the prosthetic valve can be placed in the patient using minimally invasive techniques for holding the valve in place, such as U-clips, for example, or a wide variety of other techniques and features used for minimally invasive and/or percutaneous implantation of the initial prosthetic heart valve.

The prosthetic heart valves of the disclosure may include a wide variety of different configurations, such as a prosthetic heart valve that has tissue leaflets, or a synthetic heart valve that has polymeric leaflets. In this way, the heart valves can be specifically configured for replacing any heart valve. That is, while much of the description herein refers to replacement of aortic valves, the stents (and their associated leaflets) of the disclosure can also generally be used for replacement of tricuspid valves, for use as a venous valve, or to replace a failed bioprosthesis, such as in the area of an aortic valve or mitral valve, for example.

Figure 2A:
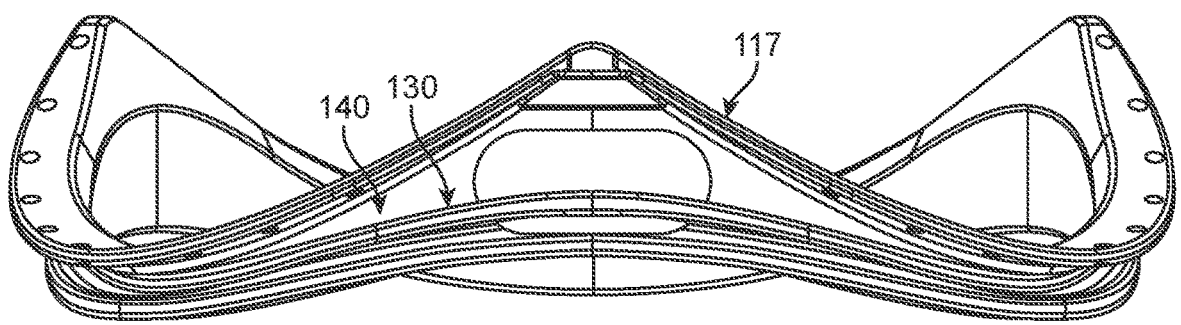
FIG. 2A is a front view of a base of the disclosure having a radiopaque element, the radiopaque element being a band extending around the base.
Figure 2B:
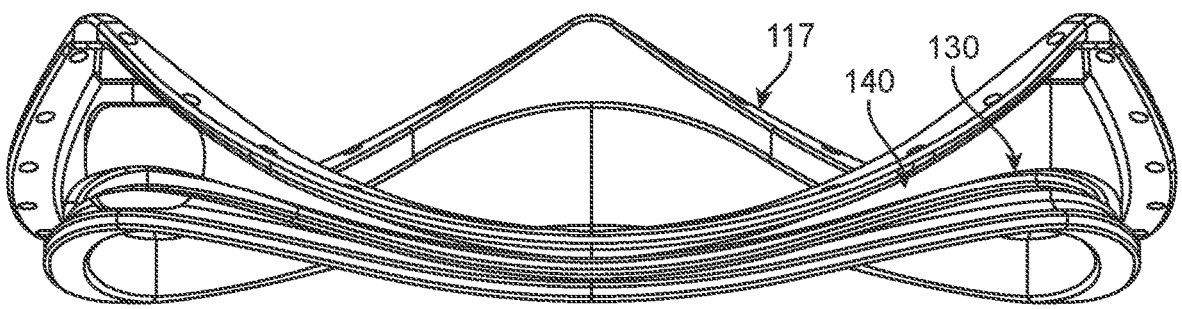
FIG. 2B is a rear view of the base of FIG. 2A.
Figure 3:
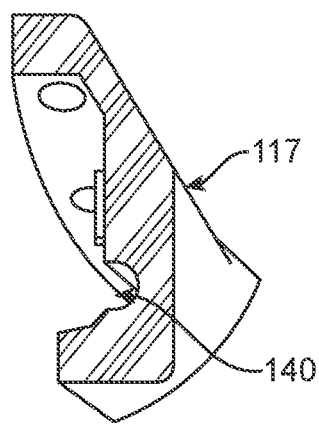
FIG. 3 is a cross-sectional view of the base of FIGS. 2A-2B.

Referring in addition to FIGS. 2A-3, embodiments of the disclosure include prosthetic heart valves similar to that of FIG. 1 that further include one or more radiopaque markers or elements that can help to facilitate accurate placement of a replacement heart valve during implantation. In the example of FIGS. 2A-2B, a base 117 of a heart valve (e.g., prosthetic heart valve 10) is provided with a radiopaque element 130. To provide radiopaque properties, the radiopaque element 130 can be made of a material including platinum, platinum iridium, other platinum alloys, gold, silver, tantalum, tungsten, cobalt chromium alloys, stainless steel, nitinol, for example. Also, a non-radiopaque material could be coated with a radiopaque material to provide radiopacity. In one example, the radiopaque element 130 is in wire form and extends within an annular groove 140 provided in an exterior surface of the base 117 around the circumference of the base 117 (see, in particular, FIG. 3). In one example, the wire forming at least a portion of the radiopaque element 130 has a diameter in a range of 0.001 to 0.010 inches. In another example, the wire 130 has a diameter of 0.003 to 0.005 inches. In one embodiment, the wire 130 is in a resilient, coiled configuration, having its ends connected together, via welding or the like, to form a closed loop. Because of the coil structure, the radiopaque element 130 can stretch and flex, allowing it to be installed within the groove 140 around the base 117. In one example, the coil diameter is in a range of 0.005 to 0.050 inches. In yet another example, the coil diameter is in a range of 0.015 to 0.020 inches. In various embodiments, the coil form of the radiopaque element 130 is not circular and is flattened (i.e. each coil is oblong).

In some embodiments, multiple radiopaque elements 130 are provided in the base 117. In one example, the number of radiopaque elements 130 (e.g., wire coils) indicates a size of the prosthetic heart valve 10. For example, one radiopaque element extending around the base 117 can indicate a 19 mm prosthetic heart valve, two radiopaque elements extending around the base 117 could indicate a 21 mm prosthetic heart valve, and so on, etc.). In this way, the size of a previously implanted prosthetic valve can be identified via fluoroscopy to be used in the selection of an appropriate replacement prosthetic valve. The base 117 and radiopaque element(s) 130 of FIGS. 2A-2B can be incorporated into the valve 10 of FIG. 1 and will function similarly except as explicitly stated.

Figure 4:
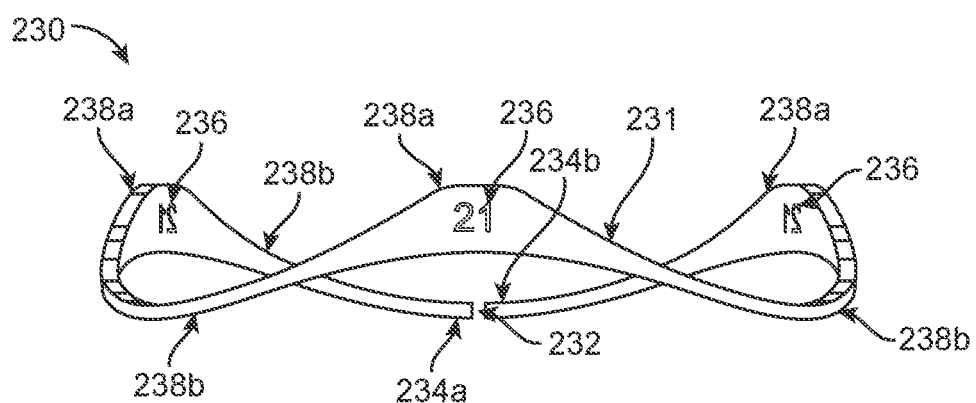
FIG. 4 is a front view of an alternate radiopaque element.

Referring now in addition to FIG. 4, which illustrates an alternative radiopaque element 230 for positing around a base (e.g., base 117) as with the embodiment of FIGS. 2A-2B. In this embodiment, the radiopaque element 230 can be described as a band configured to extend substantially around the base, within the groove. The radiopaque element 230 can include a gap 232 (i.e. may be semi-circular and not be a closed loop of material) between two ends 234a, 234b so that the radiopaque element 230 can be positioned around the base. In one example, the radiopaque element 230 includes one or more indicators 236 (e.g., three indicators spaced around the radiopaque element 230) that provide indicia relevant to the size of the prosthetic heart valve in which the radiopaque element is incorporated, for example. Additionally, the indicia could provide information regarding the position of the valve (e.g., "a" for aortic) or other information such as the model number or manufacture date of the valve. It will be understood that "one indicator" may include multiple portions such as two cutouts or areas of removed material to form a single number (e.g., 2 and 1, as shown in FIG. 4 to form "21"). The indicators 236 can be cutout portions of the material forming the radiopaque element 230 or can otherwise be made of non-radiopaque material so that the indicators 236 will be seen as contrast with respect to the other portions of the radiopaque element 230 under fluoroscopy. In one example, the radiopaque element 230 includes a generally circular body 231 forming the gap 232. Along the body 231 are three areas of increased width 238a separated by thinner connecting portions 238b. In each area of increased width 238a, an indicator 236 is stamped, machined, cut or electrochemically etched out of the body 231 or otherwise formed to provide contrast with the body 231. The indicator 236 can represent the size of the prosthetic heart valve or model number of the prosthetic heart valve, for example. The radiopaque element 230 can be made of any of the materials listed above. The radiopaque element 230 of FIG. 4 can be utilized with the base 117 of FIGS. 2A-2B can be incorporated into the valve 10 of FIG. 1 and will function similarly except as explicitly stated. A non-radiopaque material could be selectively coated with radiopaque materials in specific regions to identify key zones of the prosthetic heart valve (e.g., inter-commissural openings) or information (stent height, width, stent or orifice inside diameter, etc.) that is important for delivering subsequent transcatheter therapies such as preferential landing zones for coronary stents or percutaneous heart valves.

Figure 5:
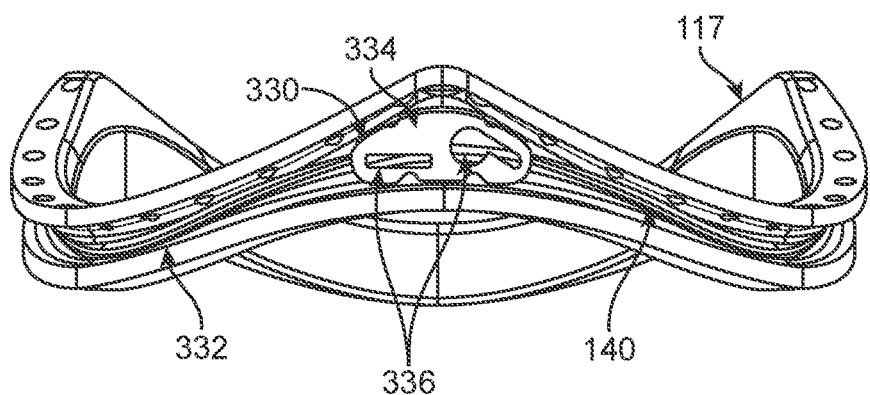
FIG. 5 is a front view of another alternate radiopaque element secured to the base of FIGS. 2A-2B.

Referring now in addition to FIG. 5, which illustrates yet another radiopaque element 330 positioned within the base 117 of FIGS. 2A-2B. In this embodiment, the radiopaque element 330 includes a wire 332 wrapped around the groove 140 of the base 117. The wire 332 is threaded through a badge 334 to support and maintain the badge 334 on the base 117. In one example, the wire 332 is made of a radiopaque material. The badge 334 is made of a radiopaque material, such as any of those disclosed herein, and includes an indicator 336. As with the prior embodiment, the indicator 336 can be stamped, machined, cut or electrochemically etched out of the badge 334 or can be made of a non-radiopaque material as to provide contrast and be visible under fluoroscopy. The base 317 and radiopaque element(s) 330 of FIG. 5 can be incorporated into the valve 10 of FIG. 1 and will function similarly except as explicitly stated.

Figure 6:
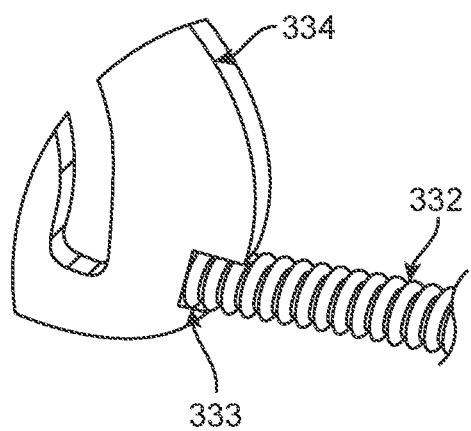
FIG. 6 is a perspective view of yet another alternate radiopaque element.
Figure 7:
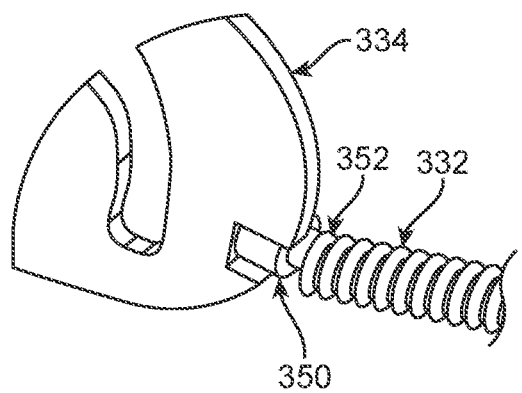
FIG. 7 is a schematic illustration of one way in which a badge of a radiopaque element can be secured to a band.
Figure 8:
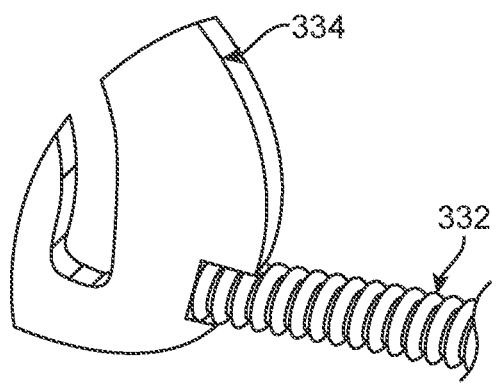
FIG. 8 is a schematic illustration of one way in which a badge of a radiopaque element can be secured to a band.

The wire 332 of FIG. 5 can be of any wire configuration disclosed herein and thus, can be secured to the badge 334 in any manner disclosed herein. In on example, the wire 332 is configured as disclosed with respect to radiopaque element 130, disclosed above. FIG. 6, for example, illustrates one method of securing the wire 332 (which may or may not be coiled) to the badge 334. At ends of the wire 332, the wire 332 is welded to itself to create a solid, joined end 333. The joined end 333 is then welded to the badge 234. The joined end 333 of the wire 332 can be deformed to create different shapes. In one embodiment, the badge 334 may include slots (not shown) to assist in welding the badge 334 to the wire 332. Alternatively, as shown in FIG. 7, a coupler 350 is provided that is welded to both the badge 334 and the wire 332 to join ends of the wire. The coupler 350 can, for example, be a metal cylinder. FIG. 8, for example, illustrates how the wire 332 can be directly welded to the badge 334. It is envisioned that the wire can be secured to the badge in other ways such as threaded the wire through a hole or similar feature on the badge (not shown) or by crimping, bonding, or suturing the wire onto the badge (also not shown).

Figure 9:
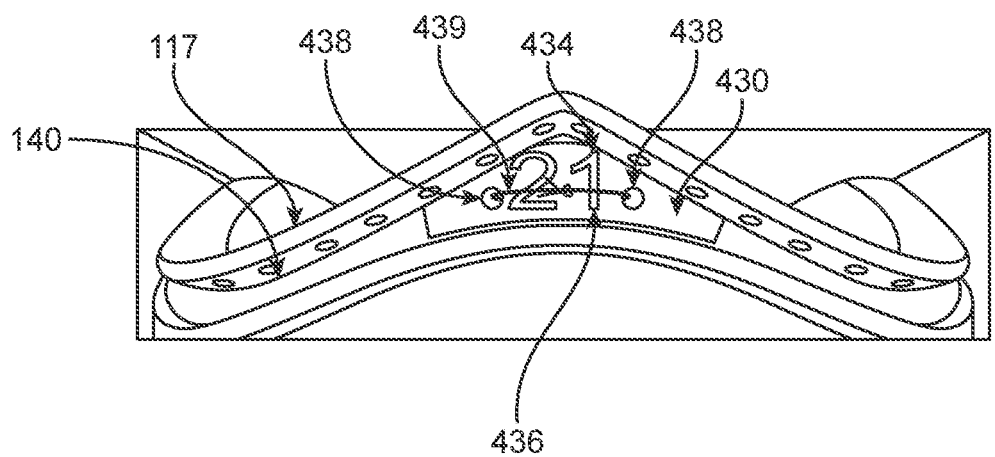
FIG. 9 is a schematic illustration of one way in which a badge of a radiopaque element can be secured to a band.

Referring now in addition to FIG. 9, which illustrates an alternate radiopaque element 430 secured within the base 117. In this embodiment, the radiopaque element 430 has a badge 434 that is made of any radiopaque material disclosed herein and includes an indicator 436, which can be configured similar to any disclosed herein. In this embodiment, the radiopaque element 430 is sewn into the base 117. In one example, the radiopaque element 430 may include one or more apertures 438 for threading one or more securing threads 439. In other embodiments, the thread 439 can be threaded through indicator 436 in the case where the indicator 436 has been formed by punched material. It will be understood that "thread" may include any flexible, elongated material suitable for securing the radiopaque element 430 to the base 117. Multiple radiopaque elements 430 can optionally be provided around the base 117, as desired. In one example, one radiopaque element 430 is provided at the base 117 proximate each commissure 16. The base 117 and radiopaque element(s) 430 of FIG. 9 can be incorporated into the valve 10 of FIG. 1 and will function similarly except as explicitly stated.

Is envisioned that one badge and/or indicator of the disclosure is positioned at each corresponding stent post (i.e. below each stent post when the prosthetic heart valve is oriented as shown in FIG. 1).

All embodiments of the disclosure can include additional radiopaque elements to assist in valve placement, as desired. For example, radiopaque elements as known in the art or disclosed herein can be placed in the stent posts, as desired. Utilizing radiopaque elements in the stent posts aids in assessing the risk of coronary artery obstruction after the prosthetic heart valve is implanted. Visualization of the stent base is important to determine proper prosthetic heart valve implant depth. Father, visualization of a surgical size of a prior implanted prosthetic heart valve aids in the selection of a further replacement prosthetic heart valve size.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A prosthetic heart valve comprising:
   a stent structure forming a plurality of commissure posts;
   a valve structure supported by the stent structure, the valve structure having an inflow end and an outflow end;
   a base supporting the stent structure, the base having a first end at the inflow end and an opposing, second end adjacent the plurality of commissure posts; the base further including a groove recessed within a material of the base between the first and second ends of the base and spanning at least two of the plurality of commissure posts; and
   a radiopaque element positioned around the base, within the groove,
   wherein the radiopaque element includes a wire extending around the base,
   wherein the wire is coiled,
   wherein the coil is flattened.

2. The prosthetic heart valve of claim 1, wherein the wire forming the coil has a diameter in the range of 0.001-0.010 inches.

3. The prosthetic heart valve of claim 1, wherein the radiopaque element includes a badge connected to the wire.

4. The prosthetic heart valve of claim 1, wherein the radiopaque element includes a badge having an indicator.

5. The prosthetic heart valve of claim 4, wherein the indicator is formed by a cutout portion of the badge.

6. The prosthetic heart valve of claim 4, wherein the badge is aligned with one commissure post of the stent structure.

7. The prosthetic heart valve of claim 4, wherein the badge is sewn to the base.

8. The prosthetic heart valve of claim 1, wherein the base is independently formed with respect to the stent structure.

\* \* \* \* \*